(12) United States Patent
Inoue et al.

(10) Patent No.: US 10,473,571 B2
(45) Date of Patent: Nov. 12, 2019

(54) TEST PIECE FOR TENSILE TESTING AND TENSILE TESTING METHOD

(71) Applicant: IHI Corporation, Tokyo (JP)

(72) Inventors: Hisato Inoue, Tokyo (JP); Masahiro Takanashi, Tokyo (JP)

(73) Assignee: IHI Corporation, Tokyo (JP)

( * ) Notice: Subject to any disclaimer, the term of this patent is extended or adjusted under 35 U.S.C. 154(b) by 73 days.

(21) Appl. No.: 15/810,219

(22) Filed: Nov. 13, 2017

(65) Prior Publication Data

US 2018/0067026 A1 Mar. 8, 2018

Related U.S. Application Data

(63) Continuation of application No. PCT/JP2016/054881, filed on Feb. 19, 2016.

(30) Foreign Application Priority Data

Aug. 19, 2015 (JP) .................................. 2015-161979

(51) Int. Cl.
*G01N 3/00* (2006.01)
*G01N 3/08* (2006.01)

(52) U.S. Cl.
CPC ....... *G01N 3/08* (2013.01); *G01N 2203/0017* (2013.01); *G01N 2203/0067* (2013.01); *G01N 2203/0252* (2013.01); *G01N 2203/0272* (2013.01); *G01N 2203/0435* (2013.01)

(58) Field of Classification Search
CPC ... G01N 2203/0017; G01N 2203/0067; G01N 2203/0252; G01N 2203/0272; G01N 2203/0435

USPC .............................................. 73/862
See application file for complete search history.

(56) References Cited

U.S. PATENT DOCUMENTS

| | | | | |
|---|---|---|---|---|
| 5,144,844 A | * | 9/1992 | Mathiak | G01N 3/04 73/794 |
| 7,204,160 B1 | * | 4/2007 | Sadegh | G01N 3/10 73/862.041 |
| 2007/0199924 A1 | | 8/2007 | Yoshida et al. | |
| 2012/0247221 A1 | * | 10/2012 | Shen | G01N 3/08 73/827 |

(Continued)

FOREIGN PATENT DOCUMENTS

| | | |
|---|---|---|
| JP | 62-108852 U | 7/1987 |
| JP | 09-079919 | 3/1997 |

(Continued)

OTHER PUBLICATIONS

International Search Report dated May 10, 2016 in PCT/JP2016/054881 filed Feb. 19, 2016 (with English Translation).

(Continued)

*Primary Examiner* — Max H Noori
(74) *Attorney, Agent, or Firm* — Oblon, McClelland, Maier & Neustadt, L.L.P.

(57) ABSTRACT

A test piece includes a tensile testing part and load applying pieces that are respectively connected to sides of the tensile testing part. Grooves are formed on bottom surfaces of the load applying pieces. Grooves are formed on upper surfaces of the load applying pieces. These grooves respectively partition the upper and lower surfaces of the tensile testing part and the load applying pieces.

5 Claims, 7 Drawing Sheets

(56) References Cited

U.S. PATENT DOCUMENTS

| | | | |
|---|---|---|---|
| 2013/0220024 A1* | 8/2013 | Osborne | G01M 5/005 |
| | | | 73/849 |
| 2018/0095019 A1* | 4/2018 | Li | G01N 3/08 |
| 2019/0072467 A1* | 3/2019 | Iwamoto | G01N 3/08 |

FOREIGN PATENT DOCUMENTS

| | | |
|---|---|---|
| JP | 2004-163276 | 6/2004 |
| JP | 2006-258454 | 9/2006 |
| JP | 4150383 | 9/2008 |
| JP | 2014-074655 | 4/2014 |
| JP | 2014-228290 | 12/2014 |
| JP | 2015-090355 | 5/2015 |

OTHER PUBLICATIONS

Written Opinion dated May 10, 2016 in PCT/JP2016/054881 filed Feb. 19, 2016.

* cited by examiner

TEST PIECE FOR TENSILE TESTING AND TENSILE TESTING METHOD

CROSS REFERENCE TO RELATED APPLICATIONS

This application is a continuation application of International Application No. PCT/JP2016/054881, filed on Feb. 19, 2016, which claims priority to Japanese Patent Application No. 2015-161979, filed on Aug. 19, 2015, the entire contents of which are incorporated by reference herein.

BACKGROUND

1. Technical Field

The present disclosure relates to tensile testing of a material.

2. Description of the Related Art

Conventionally, a method in which both ends of a test piece in a pulling direction are adhered to a pair of pulling jigs of a testing apparatus, the jigs are separated from each other in the pulling direction to apply a tensile force on the test piece in the pulling direction is known in the art as a method for testing the tensile strength of a material. With this method, however, it is difficult to carry out a test assuming that the material could be used in a high-temperature environment in which the adhesive agent will lose its adhesive force.

Therefore, the existing tensile testing of materials is often carried out by not using an adhesive agent but by using a method in which both end portions of the test piece that has sufficient dimensions in the pulling direction are held with a pair of chucks of the testing apparatus and then the chucks are separated from each other in the pulling direction to apply the tensile force on the test piece in the pulling direction (see Japanese Patent Application Laid-Open No. 2014-74655).

SUMMARY

In the fiber-reinforced composite materials, for example, such as fiber reinforced plastic (FRP), it is difficult to increase the dimensions in a direction different from the fiber direction. When tensile testing is to be carried out in the direction different from the fiber direction as the pulling direction, it is difficult to prepare a test piece in a shape suitable for the method explained above in which the test piece is held by the chucks and the tensile force is applied thereon.

Similar problem occurs during tensile testing in which the tensile force is applied between two members adhered to each other by using an adhesive agent to evaluate the adhesive strength of the two members.

The present disclosure has been made in view of the above circumstances. An object of the present disclosure is to provide a tensile testing method that can be extensively carried out under various conditions without any limitation such as materials to be tested, test environments, and the like, and a test piece for tensile testing that is suitable when implementing this tensile testing method.

According to the first aspect of the present disclosure, a test piece for tensile testing includes a tensile testing part having a three-dimensional shape that has n-fold symmetry (where "n" is an even number equal to or greater than four) around a central axis that extends in a pulling direction and; "n" number of load applying pieces that are integrally formed with the tensile testing part, and are radially connected to the tensile testing part around the central axis in a direction orthogonal to the pulling direction. The tensile testing part includes a first end portion arranged on one side in the pulling direction and a second end portion arranged on the opposite side of the first end portion in the pulling direction. The "n" number of load applying pieces are constituted by a first load applying piece and a second load applying piece. The first load applying piece is connected to a part between the first end portion and a probable rupture location of the tensile testing part, and the second load applying piece is connected to a part between the second end portion of the tensile testing part and the probable rupture location.

The first load applying piece can include an application surface that receives a load transmitted from the second end portion side toward the first end portion side; and a groove formed with a depth corresponding to the probable rupture location at a part that connects the tensile testing part and the first load applying piece, and that partitions the first load applying piece and the second end portion of the tensile testing part. The second load applying piece can include an application surface that receives a load transmitted from the probable rupture location toward the second end portion side; and a groove formed with a depth corresponding to the probable rupture location at a part that connects the tensile testing part and the second load applying piece, and that partitions the second load applying piece and the first end portion of the tensile testing part.

The first load applying piece and the second load applying piece can be alternately arranged in a circumferential direction around the central axis.

The test piece for tensile testing can be made of a fiber-reinforced composite material made with fibers as a base material. A direction in which the fibers of the fiber-reinforced composite material do not extend can be the pulling direction.

According to the second aspect of the present disclosure, a tensile testing method includes exerting a tensile force in a pulling direction on the test piece for tensile testing according to the first aspect.

According to the present disclosure, tensile testing can be extensively carried out under various conditions without any limitations of materials to be tested, test environments, and the like.

DESCRIPTION OF THE EMBODIMENTS

Figure 1:
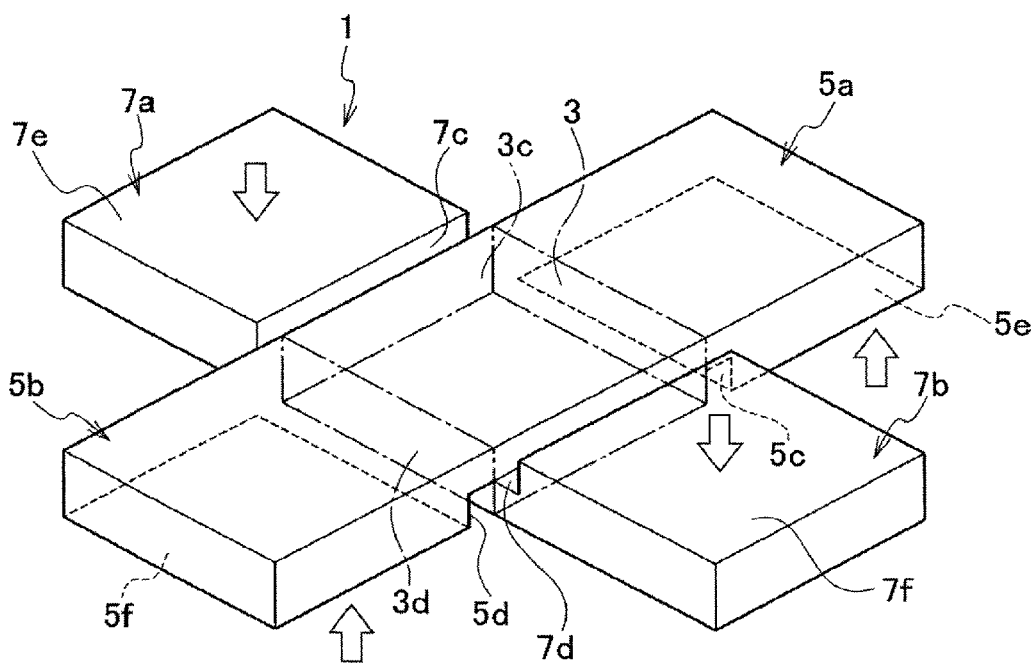
FIG. 1 is a perspective view of a test piece for tensile testing according to an embodiment of the present disclosure.

Exemplary embodiments of the present disclosure are explained below with reference to the accompanying drawings. The configuration of test pieces shown in the drawings referred to in the following embodiments is merely conceptual and the ratios of the dimensions of structural elements may not necessarily match with the actual ratios of the dimensions.

FIG. 1 is a perspective view of a test piece for tensile testing according to an embodiment of the present disclosure. As shown in FIG. 1, a test piece for tensile testing (hereinafter, "test piece") 1 according to the present embodiment includes a tensile testing part 3 that is a part enclosed with a one-dot chain line, and four load applying pieces 5a, 5b, 7a, 7b that extend in four directions from the tensile testing part 3.

Figure 2A:
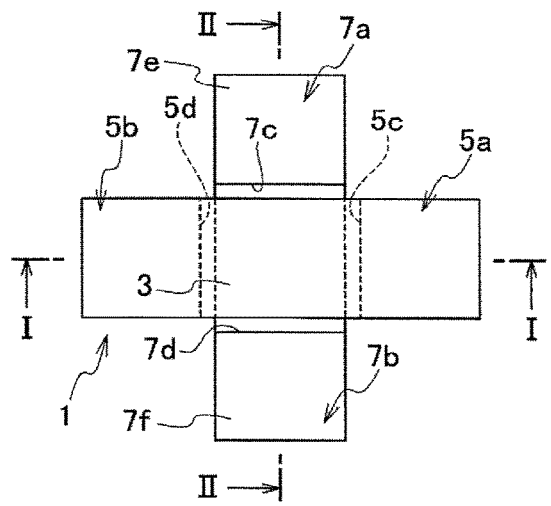
FIG. 2A is a plan view of the test piece shown in FIG. 1.
Figure 2B:
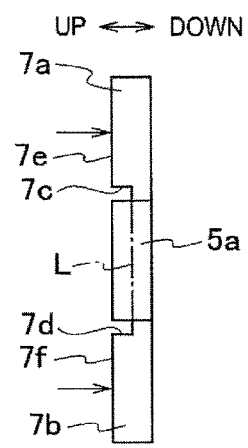
FIG. 2B is a front view of the same.
Figure 2C:
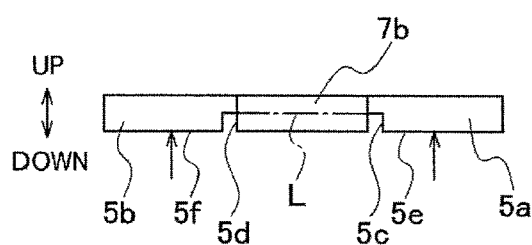
FIG. 2C is a side view of the test piece shown in FIG. 1.
Figure 2D:
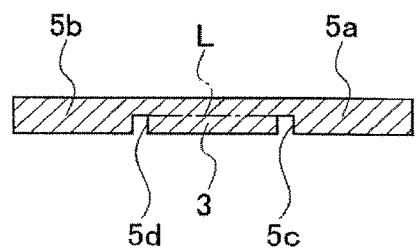
FIG. 2D is a sectional view along I-I line shown in FIG. 2A.
Figure 2E:
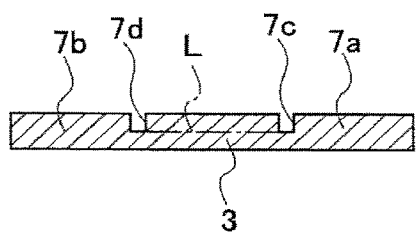
FIG. 2E is a sectional view along II-II line shown in FIG. 2A.

FIG. 2A is a plan view and FIG. 2B is a front view of the test piece shown in FIG. 1. FIG. 2C is a side view of the test piece shown in FIG. 1. FIG. 2D is a sectional view along I-I line shown in FIG. 2A, and FIG. 2E is a sectional view along II-II line shown in FIG. 2A.

As shown in FIG. 2A, the tensile testing part 3 has a square shape in a plan view, and includes a first end portion (one end portion or an upper surface) 3c in a pulling direction and a second end portion (the other end portion or a lower surface) 3d positioned opposite to the first end portion 3c in the pulling direction. The load applying pieces 5a, 5b, 7a, 7b are respectively connected to four sides of the tensile testing part 3. The tensile testing part 3 and each of the load applying pieces 5a, 5b, 7a, 7b are partitioned by grooves 5c, 5d, 7c, 7d formed on the respective load applying pieces 5a, 5b, 7a, 7b.

The load applying pieces (first load applying piece) 5a and 5b are formed so as to extend to two sides of the tensile testing part 3 that are facing each other in the right-left direction. The grooves 5c and 5d formed on the respective load applying pieces 5a and 5b partition the load applying pieces 5a and 5b and the tensile testing part 3. The load applying pieces 5a and 5b respectively include bottom surfaces (application surfaces) 5e and 5f that receive a load applied in an upward direction during the tensile testing. In other words, the load applying pieces 5a and 5b receive a load transmitted from the second end portion 3d side toward the first end portion 3c side.

As shown in FIG. 2B, the grooves 5c and 5d are formed on the bottom surfaces 5e and 5f of the load applying pieces 5a and 5b. A depth of each of the grooves 5c and 5d is defined as a distance from a bottom surface of the tensile testing part 3 to the middle in a vertical direction in accordance with a probable rupture location L shown by a one-dot chain line in FIG. 2B. The probable rupture location L is a portion of the tensile testing part that is expected to be ruptured during the tensile testing.

As shown in FIG. 2D, the tensile testing part 3 and each of the load applying pieces 5a and 5b arranged on the left and right sides thereof are connected to each other on an upper surface side of the test piece 1 above the probable rupture location L.

As shown in FIG. 2A, the load applying pieces (second load applying piece) 7a and 7b are formed so as to extend to two sides of the tensile testing part 3 that are facing each other in the back-front direction. The grooves 7c and 7d formed on the respective load applying pieces 7a and 7b partition the load applying pieces 7a and 7b and the tensile testing part 3. The load applying pieces 7a and 7b respectively include upper surfaces (application surfaces) 7e and 7f that receive a load applied in a downward direction during the tensile testing. In other words, the load applying pieces 7a and 7b receive a load transmitted from the first end portion 3c side toward the second end portion 3d side.

As shown in FIG. 2C, the grooves 7c and 7d are formed on the upper surfaces 7e and 7f of the load applying pieces 7a and 7b. A depth of each of the grooves 7c and 7d is defined as a distance from the upper surface of the tensile testing part 3 to the middle in the vertical direction in accordance with the probable rupture location L shown by a one-dot chain line in FIG. 2C.

As shown in FIG. 2E, the tensile testing part 3 and each of the load applying pieces 7a and 7b arranged on the front and back sides thereof are connected to each other on a lower surface side of the test piece 1 below the probable rupture location L.

In the present embodiment, the test piece 1 is made of a fiber-reinforced composite material having fiber as a base material such as a carbon fiber-reinforced composite material. The direction in which the base material fibers do not extend is set to the vertical direction, which is the pulling direction of the test piece 1.

As indicated by arrows in FIG. 1, in the test piece 1 according to the present embodiment, when an upward load is applied on the bottom surfaces 5e and 5f of the load applying pieces 5a and 5b arranged on the left and right sides of the tensile testing part 3, an upward force is exerted on an upper part of the tensile testing part 3 above the probable rupture location L.

In contrast, when a downward load is applied on the upper surfaces 7e and 7f of the load applying pieces 7a and 7b, a downward force is exerted on a lower part of the tensile testing part 3 below the probable rupture location L.

In this manner, across the probable rupture location L, the upward force is exerted on the upper surface side and the downward force is exerted on the lower surface side of the tensile testing part 3. Therefore, a tensile force of which the pulling direction is the vertical direction is exerted on the tensile testing part 3. Accordingly, a test for determining the tensile strength of the test piece 1 can be carried out in the tensile testing part 3.

Figure 3:
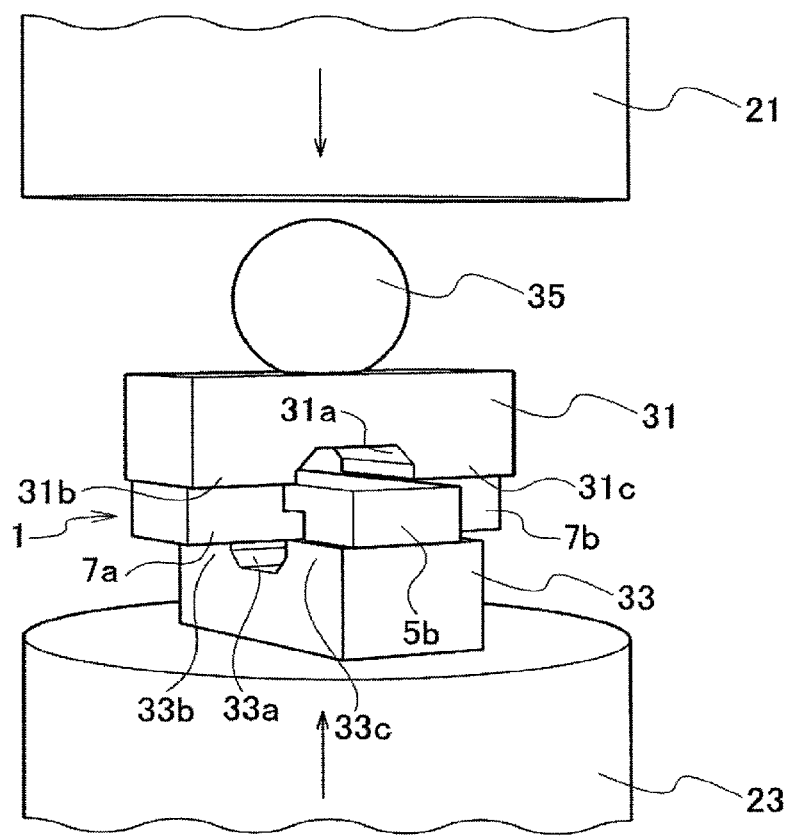
FIG. 3 is a diagram for explaining a tensile testing method according to the embodiment of the present disclosure implemented by using the test piece shown in FIG. 1.

An example in which the test piece 1 is set in a testing device and a tensile testing method according to an embodiment of the present disclosure is carried out is explained below with reference to FIG. 3. A testing device shown in FIG. 3 is typically used in a compression test in which an upper ram 21 is moved closer to a lower ram 23 to exert a compressive load on a test piece arranged between both the rams 21 and 23. In the example shown in FIG. 3, however, with also using jigs 31 and 33 and a steel ball 35, a tensile force is exerted on the test piece 1 by moving the upper ram 21 closer to the lower ram 23.

Figure 4A:
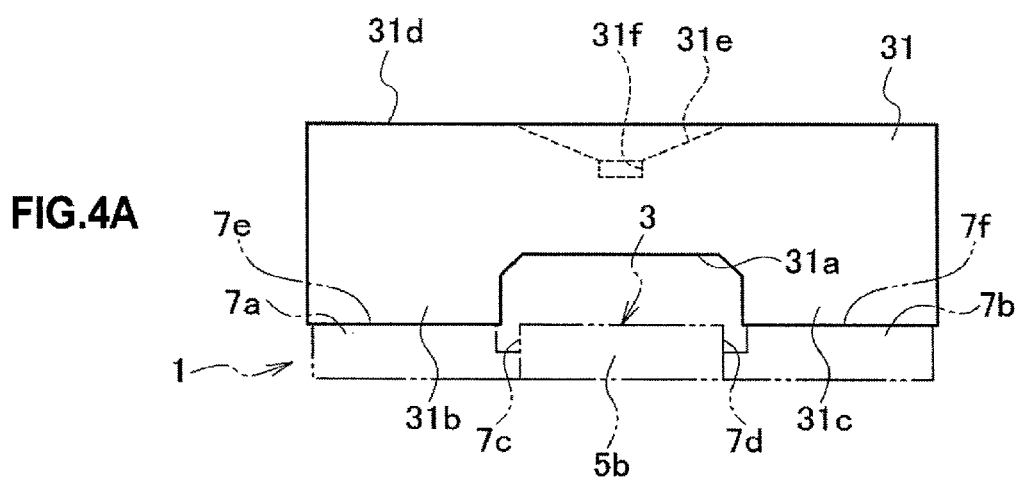
FIG. 4A is a front view of a jig used in the tensile testing shown in FIG. 3.

The jigs 31 and 33 are explained below. As shown in FIG. 4A, the upper jig 31 is placed on the test piece 1. The jig 31 includes on a lower surface thereof a concave portion 31a that straddles the tensile testing part 3 of the test piece 1. The concave portion 31*a* includes, on both sides thereof, legs 31*b* and 31*c* that are placed on the upper surfaces 7*e* and 7*f* of the load applying pieces 7*a* and 7*b* arranged on the upper and lower sides of the test piece 1.

Figure 4B:
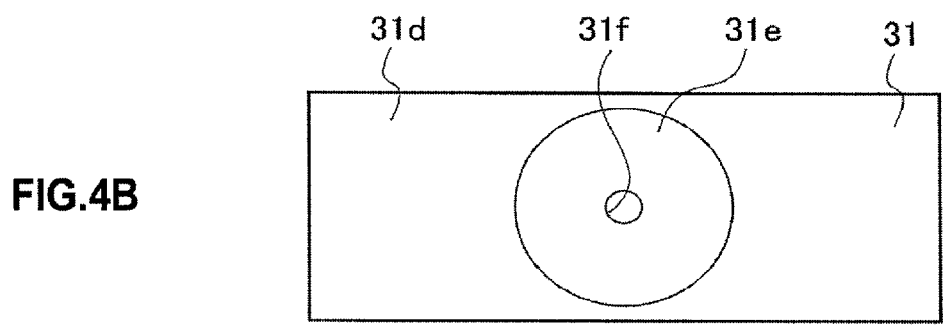
FIG. 4B is a plan view of the same.

As shown in FIG. 4B, a conical-shaped concave portion 31*e* is formed on an upper surface 31*d* of the jig 31. A cylindrical groove 31*f* is formed at the center of the concave portion 31*e*. The concave portion 31*e* is formed so as to accommodate the steel ball 35 shown in FIG. 3. The groove 31*f* is formed such that, when the steel ball 35 is accommodated in the concave portion 31*e*, a part of the steel ball 35 surface fits therein and the steel ball 35 becomes still in the concave portion 31*e*.

On the other hand, the lower jig 33 is arranged under the test piece 1. The jig 33 has a shape same as that of the upper jig 31 without the concave portion 31*e* and the groove 31*f* in a vertically inverted posture. In other words, the jig 33 has on an upper surface thereof a concave portion 33*a* that straddles the tensile testing part 3 of the test piece 1. The concave portion 33*a* includes on both sides thereof legs 33*b* and 33*c* on which the load applying pieces 5*a* and 5*b* formed on the right and left sides of the test piece 1 are placed.

When carrying out the tensile testing on the test piece 1 in the testing device shown in FIG. 3, the jig 33 is placed on the lower ram 23 while keeping the concave portion 33*a* facing upward. Furthermore, the load applying pieces 5*a* and 5*b* of the test piece 1 are placed on the legs 33*b* and 33*c*. Accordingly, the load applying pieces 5*a* and 5*b* are supported from below by the legs 33*b* and 33*c* of the jig 33. It is allowable that the legs 33*b* and 33*c* non-movably support the load applying pieces 5*a* and 5*b*.

The legs 31*b* and 31*c* of the jig 31 are placed on the upper surfaces 7*e* and 7*f* of the load applying pieces 7*a* and 7*b* while keeping the concave portion 31*a* facing downward. The steel ball 35 is then placed in the concave portion 31*e* of the jig 31 to fit a part of the steel ball 35 in the groove 31*f*. In a state in which the steel ball 35 is stationary in the concave portion 31*e*, the upper ram 21 of the testing device is brought into contact with the steel ball 35 from above.

Accordingly, in this state, the upper ram 21 of the testing device is gradually moved down closer to the lower ram 23, and a downward load is applied on the upper surfaces 7*e* and 7*f* of the load applying pieces 7*a* and 7*b* via the legs 31*b* and 31*c* of the jig 31.

Because a uniform downward load is applied on the entire jig 31 via the steel ball 35 accommodated in the concave portion 31*e*, the downward load gets uniformly applied on the upper surfaces 7*e* and 7*f* of the load applying pieces 7*a* and 7*b* via the legs 31*b* and 31*c*.

The load applying pieces 5*a* and 5*b* are supported from below by the legs 33*b* and 33*c* of the jig 33. Therefore, an upward load is uniformly applied on the load applying pieces 5*a* and 5*b* via the legs 33*b* and 33*c* of the jig 33.

Figure 5:
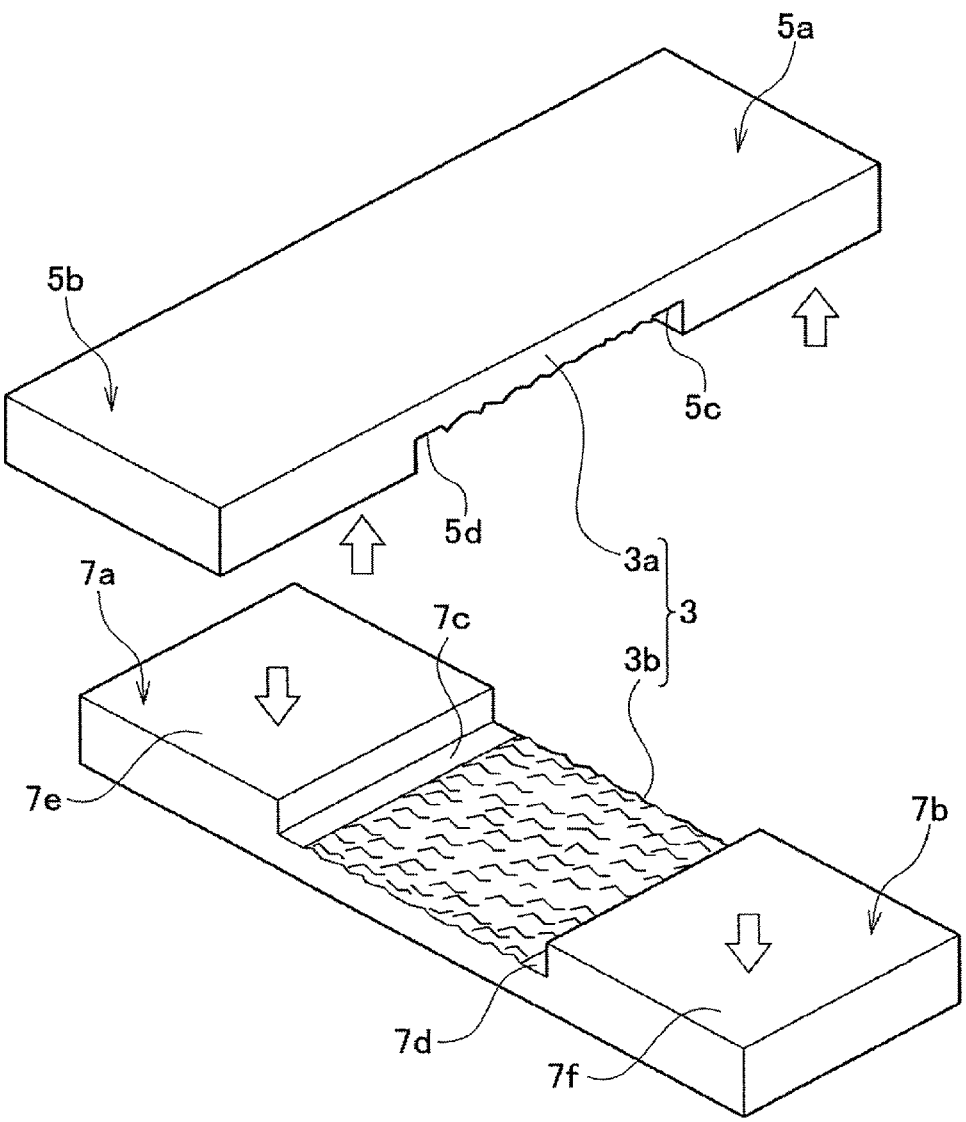
FIG. 5 is a perspective view of the test piece shown in FIG. 1 that has been ruptured in a rupture part and is split into two parts in a pulling direction during the tensile testing shown in FIG. 3.

As a result, the upward force is transmitted from the load applying pieces 5*a* and 5*b* to a part of the tensile testing part 3 on the upper surface 3*c* side than the probable rupture location L, and the downward force is transmitted from the load applying pieces 7*a* and 7*b* to a part of the tensile testing part 3 on the lower surface 3*d* side than the probable rupture location L. In other words, the testing device exerts a tensile force in the vertical direction on the tensile testing part 3. If this tensile force exceeds the strength of the tensile testing part 3, the tensile testing part 3 ruptures into upper and lower two parts at the probable rupture location L, and splits into an upper portion 3*a* and a lower portion 3*b* as shown in FIG. 5.

In the test piece 1 according to the present embodiment, the load applying pieces 5*a*, 5*b*, 7*a*, 7*b* that are integrally formed with the tensile testing part 3 are connected to the four sides of the tensile testing part 3 that has a square shape in a plan view. The grooves 5*c* and 5*d* are formed on the bottom surfaces 5*e* and 5*f* of the load applying pieces 5*a* and 5*b*, and the grooves 7*c* and 7*d* are formed on the upper surfaces 7*e* and 7*f* of the load applying pieces 7*a* and 7*b*. These grooves respectively partition the upper and lower surfaces of the tensile testing part 3 and the load applying pieces 5*a*, 5*b*, 7*a*, 7*b*.

Accordingly, when the upward load from the bottom surfaces 5*e* and 5*f* of the load applying pieces 5*a* and 5*b* is applied and the downward load from the upper surfaces 7*e* and 7*f* of the load applying pieces 7*a* and 7*b* is applied, by the force transmitted to the tensile testing part 3 from each of the load applying pieces 5*a*, 5*b*, 7*a*, 7*b*, the vertical tensile force can be exerted on the tensile testing part 3 across the probable rupture location L.

Accordingly, the vertical tensile force can be exerted on the tensile testing part 3 even if the upper and lower ends 3*c* and 3*d* of the test piece 1 are not adhered to the testing device with an adhesive agent. Therefore, the tensile testing can be carried out even in a high-temperature environment in which the adhesive agent loses its adhesive force.

Moreover, the vertical tensile force can be exerted on the tensile testing part 3 even if the upper and lower ends 3*c* and 3*d* of the test piece 1 are not held by using chucks of the testing device. Therefore, according to the present embodiment, for example, by forming the test piece 1 by using a fiber-reinforced composite material having fiber as a base material such as a carbon fiber-reinforced composite material, even if it is structurally difficult to form portions that can be held by the chucks at both ends in the vertical direction of the test piece 1 in which base material fibers do not extend, the tensile testing can be carried out.

According to the test piece 1 of the present embodiment, each of the load applying pieces 5*a*, 5*b*, 7*a*, 7*b* is connected to the tensile testing part 3 along the extension direction of the base material fibers. In other words, the base material fibers that constitute the test piece 1 continuously extend from the tensile testing part 3 to each of the load applying pieces 5*a*, 5*b*, 7*a*, 7*b*. Accordingly, the strength of the portion of the grooves 5*c*, 5*d*, 7*c*, 7*d* in which the tensile testing part 3 and the load applying pieces 5*a*, 5*b*, 7*a*, 7*b* are respectively connected increases because of the reinforcement of fibers provided by the reinforced material. Therefore, the possibility of the connecting portion between the tensile testing part 3 and each of the load applying pieces 5*a*, 5*b*, 7*a*, 7*b* getting disconnected by a shear force generated by the load applied on each of the load applying pieces 5*a*, 5*b*, 7*a*, 7*b* decreases.

Consequently, when the vertical tensile force is exerted on the tensile testing part 3 by applying the upward load transmitted from the load applying pieces 5*a* and 5*b* to the upper part of the tensile testing part 3 above the probable rupture location L and the downward load transmitted from the load applying pieces 7*a* and 7*b* to the lower part of the tensile testing part 3 below the probable rupture location L, actively breaking the tensile testing part 3 into two and separating the tensile testing part 3 at the probable rupture location L in the vertical direction in which the fibers do not extend becomes easy.

Therefore, by configuring the test piece and the testing method such that it is easy to separate by rupturing the tensile testing part 3 in the pulling direction with the load applied to the load applying pieces 5a, 5b, 7a, 7b, the tensile testing can be carried out easily.

In the embodiment explained above, the test piece 1 in which the tensile testing part 3 has a square shape in a plan view, and the four load applying pieces 5a, 5b, 7a, 7b are connected to four sides of the tensile testing part 3 is explained.

Figure 6:
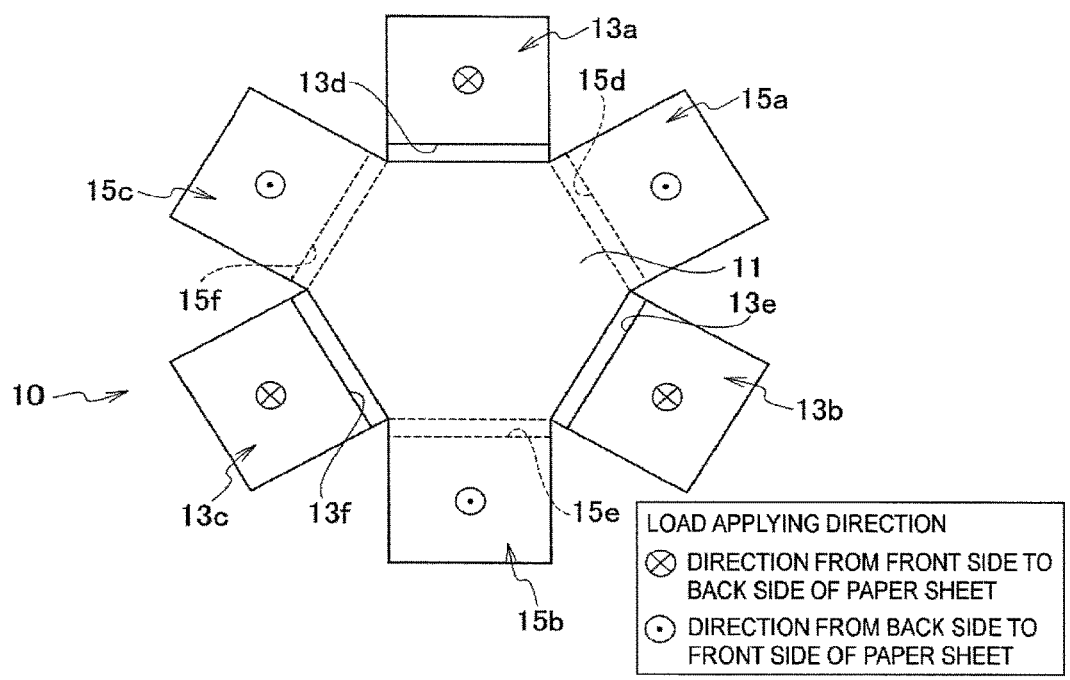
FIG. 6 is a plan view of a test piece for tensile testing according to another embodiment of the present disclosure.

However, for example, as depicted in a test piece 10 shown in FIG. 6, a tensile testing part 11 can have a regular hexagonal shape in a plan view, and six load applying pieces 13a, 13b, 13c, 15a, 15b, 15c can be respectively connected to six sides of the tensile testing part 11. In such a configuration, grooves 13d, 13e, 13f are respectively formed on an upper surface side of every alternate load applying pieces 13a, 13b, 13c to partition the load applying pieces 13a, 13b, 13c and an upper surface of the tensile testing part 11, and grooves 15d, 15e, 15f are respectively formed on a lower surface side of the other every alternate load applying pieces 15a, 15b, 15c to partition the load applying pieces 15a, 15b, 15c and a lower surface of the tensile testing part 11.

Accordingly, when carrying out tensile testing on the test piece 10, a load is applied on each of the load applying pieces 13a, 13b, 13c, 15a, 15b, 15c from the surfaces on which the grooves 13d, 13e, 13f, 15d, 15e, 15f are formed. With this configuration, the vertical tensile force can be exerted on the tensile testing part 11, and tensile testing similar to the one carried out on the test piece 1 explained in the previous embodiment can be carried out.

In such a configuration, the shape in a plan view of the tensile testing part of the test piece is not limited to the square or the regular hexagon as explained above, and can be a regular n-sided polygon (however, "n" is an even number equal to or greater than four) such as a regular octagon or a regular decagon. In other words, the tensile testing part can include connecting surfaces to connect with each of the load applying pieces, and each of the connecting surfaces can have a plane surface that has n-fold symmetry. In such a configuration, each of the load applying pieces is connected radially from each of the sides of the tensile testing part around a central axis (axis of rotational symmetry) of the tensile testing part, which extends in the pulling direction. In other words, the first load applying piece and the second load applying piece of the present embodiment are alternately arranged in the circumferential direction around the central axis of the tensile testing part. With this configuration, the test piece has a three-dimensional shape that has an n-fold symmetry (however, "n" is an even number equal to or greater than four) around the central axis that extends in the pulling direction.

Even if the test piece is configured in this manner, same results as that with the test pieces 1 and 10 explained in the above embodiments can be obtained. By increasing "n" to infinity, the outer shape of the tensile testing part can be formed in a shape that is closer to a perfect circle. In such a configuration, as long as the uniformity of the force exerted on the tensile testing part from the load applying pieces is within an allowable range, the connecting surfaces explained above can be curved surfaces.

Figure 7:
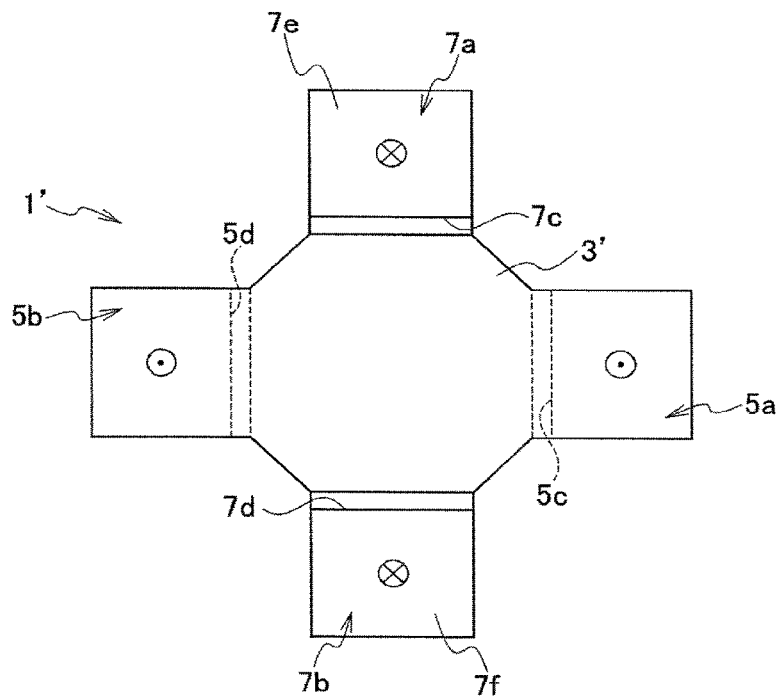
FIG. 7 is a plan view of a test piece for tensile testing according to yet another embodiment of the present disclosure.
Figure 8A:
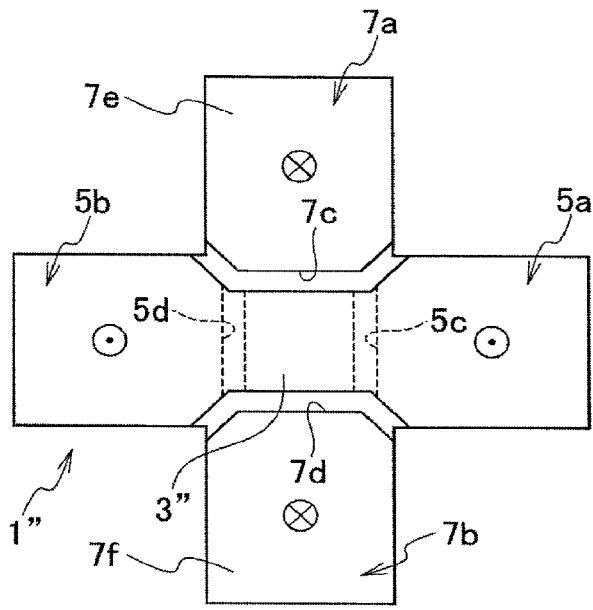
FIG. 8A is a plan view of a test piece for tensile testing according to yet another embodiment of the present disclosure.
Figure 8B:
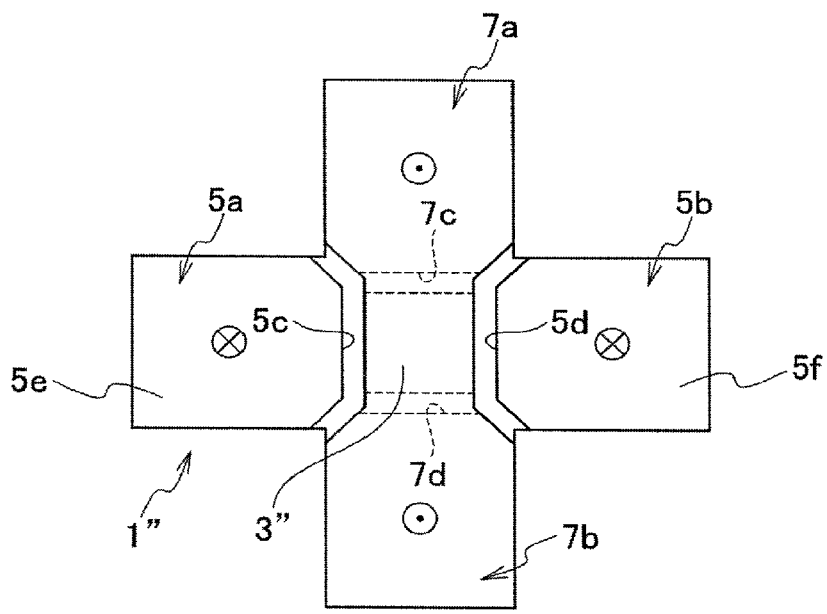
FIG. 8B is a bottom view of the same.

Similar to a test piece 1' shown in FIG. 7, it is allowable that the outer shape of a tensile testing part 3' is wider than the outer shape of the tensile testing part 3 shown in FIG. 2A. Alternatively, similar to a test piece 1" shown in FIGS. 8A and 8B, it is allowable that grooves 5c, 5d, 7c, 7d of load applying pieces 5a, 5b, 7a, 7b extrude inwardly and the outer shape of a tensile testing part 3" is narrower than the tensile testing part 3 shown in FIG. 2A.

In the present embodiments, the direction of the load applied on each of the load applying pieces is alternately reversed in the circumferential direction of the tensile testing part (the central axis of the tensile testing part). In other words, a load in the same direction is alternately applied on the load applying pieces 5a, 5b, 7a, 7b (13a, 13b, 13c, 15a, 15b, 15c). However, as long as the direction of the tensile force exerted on the tensile testing part 3, 3', 3", 11 via each of the load applying pieces 5a, 5b, 7a, 7b, 13a, 13b, 13c, 15a, 15b, 15c is vertical, it is allowable to arbitrarily apply upward and downward loads on any of the load applying pieces 5a, 5b, 7a, 7b, 13a, 13b, 13c, 15a, 15b, 15c.

Instead of the fiber-reinforced composite material, the present disclosure is applicable to a test piece used for testing the tensile strength of other materials. The present disclosure is also applicable to a test piece used for testing the adhesive strength of a material constituted by adhering two members using an adhesive agent.

When testing the adhesive strength between two members adhered by using an adhesive agent, the tensile testing part is formed by using the two members adhered by using the adhesive agent, a first load applying piece that extends to the tensile testing part is constituted by one of the two members, and a second load applying piece that extends to the tensile testing part is constituted by the other member. Therefore, by applying loads in opposite directions to the load applying pieces, the tensile force can be exerted in a direction in which the two members adhered together by using the adhesive agent to constitute the tensile testing part are peeled off from each other.

Effects and advantages according to the present embodiment are explained below.

In the part between the first end portion (one end portion) in the pulling direction of the tensile testing part and the probable rupture location (the rupture part), the load applied on the first load applying piece connected to this part acts as a force transmitted from the second end portion (the other end portion, the probable rupture location, and the rupture part) toward the first end portion (one end portion). On the other hand, in the part between the second end portion (the other end portion) in the pulling direction of the tensile testing part and the probable rupture location (the rupture part), the load applied on the second load applying piece connected to this part acts as a force transmitted from the first end portion (the probable rupture location, the rupture part) toward the second end portion (the other end portion).

Therefore, for example, in a state in which the first load applying piece is fixed, when a load transmitted from the first end portion side toward the second end portion side is applied on the remaining second load applying piece, the tensile force in the pulling direction is exerted on both the parts on the first end portion side and the second end portion side of the tensile testing part. In other words, depending on how the load is applied on each load applying piece, the tensile testing can be carried out with the same operation as that of the compression testing.

In such tensile testing carried out in the same manner as the compression testing, to exert the tensile force on the tensile testing part, it is not necessary to pull the tensile testing part from both sides in the pulling direction. Therefore, it is not necessary to adhere the pulling jig of the testing apparatus to the test piece by using an adhesive agent and to hold both ends of the test piece in the pulling direction with chucks. Moreover, it is not necessary to increase the dimensions of the test piece in the pulling direction to a certain extent for securing a space for the holding by the chucks.

Therefore, even if a material to be tested is such that increasing the dimensions in the pulling direction is difficult, or testing at a high temperature is required because the usage environment thereof is a high-temperature environment, the tensile testing can still be carried out regardless of materials and test environments.

The first load applying piece includes the application surfaces on which the load transmitted from the second end portion side (the probable rupture location, the rupture part) toward the first end portion side of the tensile testing part is applied. The application surfaces are arranged adjacent to the second end portion of the tensile testing part that is partitioned by the grooves. Similarly, the second load applying piece includes the application surfaces on which the load transmitted from the first end portion side (the probable rupture location, the rupture part) toward the second end portion side of the tensile testing part is applied. The application surfaces are arranged adjacent to the first end portion of the tensile testing part that is partitioned by the grooves.

Accordingly, the end portions of the tensile testing part and the application surfaces of the load applying pieces arranged adjacent to the end portions are positioned on the same plane. Moreover, by forming the grooves with a depth corresponding to the rupture part between the end portions and the application surfaces, the test piece can be formed in a state in which the load applying pieces are connected to the tensile testing part. Because no end portions of the tensile testing part exist in front of the application surfaces in the pulling direction, interference with the end portions of the tensile testing part can be easily avoided and the load can be applied on the application surfaces of the load applying pieces.

By applying in uniform balance on the "n" number of load applying pieces the load transmitted from the probable rupture location (the rupture part) toward the first end portion side of the tensile testing part and the load transmitted from the probable rupture location (the rupture part) toward the second end portion side of the tensile testing part, a tensile force in the pulling direction can be precisely exerted on the tensile testing part.

Generally, when a test piece for tensile testing is made of a fiber-reinforced composite material, forming the test piece in larger dimensions in a direction in which the base material fibers do not extend is structurally difficult.

Therefore, when a direction in which the base material fibers do not extend is the pulling direction, it is difficult to form holding portions for exerting the tensile force and the like in an appropriate size on both ends in the pulling direction of the test piece for tensile testing.

However, according to the present embodiments, by distributing on the "n" number of load applying pieces the load transmitted from the probable rupture location (the rupture part) toward the first end portion side of the tensile testing part and the load transmitted from the probable rupture location (the rupture part) toward the second end portion side of the tensile testing part, the tensile force in the pulling direction can be exerted on the tensile testing part.

Therefore, even if the base material fibers do not extend in the pulling direction, the tensile force in the pulling direction can be exerted on the tensile testing part and the tensile testing can be carried out appropriately.

Each of the load applying pieces is connected to the tensile testing part along the extension direction of the fibers. In other words, the tensile testing part and the load applying pieces are integrally formed along the extension direction of the fibers. With this configuration, strength of the connecting portion between each of the load applying pieces and the tensile testing part increases because of the reinforcement of fibers provided by the reinforced material. Accordingly, the possibility of the connecting portion between the tensile testing part and each of the load applying pieces getting disconnected because of the shear force generated when the load is applied on each of the load applying pieces decreases.

Therefore, when the tensile force in the pulling direction is exerted on the tensile testing part by applying a load transmitted from the first load applying piece to a part of the tensile testing part on the first end portion side of the rupture part and a load in an opposite direction transmitted from the second load applying piece to a part of the tensile testing part on the second end portion side of the rupture part, the tensile testing part can be easily separated from the probable rupture location (the rupture part) in the pulling direction in which fibers do not extend.

Therefore, by configuring the test piece and the testing method such that it is easy to separate the tensile testing part by rupturing the tensile testing part in the pulling direction with the load applied to the load applying pieces, the tensile testing can be easily carried out.

The tensile testing method according to the present disclosure can also be implemented in testing devices other than the testing device shown in FIG. 3 in the embodiments explained above.

What is claimed is:

1. A test piece for tensile testing comprising:
    a tensile testing part having a three-dimensional shape that has n-fold symmetry (where "n" is an even number equal to or greater than four) around a central axis that extends in a pulling direction and;
    "n" number of load applying pieces that are integrally formed with the tensile testing part, and are radially connected to the tensile testing part around the central axis in a direction orthogonal to the pulling direction, wherein
    the tensile testing part includes a first end portion arranged on one side in the pulling direction and a second end portion arranged on the opposite side of the first end portion in the pulling direction, and
    the "n" number of load applying pieces are constituted by a first load applying piece and a second load applying piece, wherein
    the first load applying piece is connected to a part between the first end portion of the tensile testing part and a probable rupture location of the tensile testing part,
    the second load applying piece is connected to a part between the second end portion of the tensile testing part and the probable rupture location,
    the first load applying piece includes
        an application surface that receives a load transmitted from the second end portion side toward the first end portion side; and
        a groove formed with a depth corresponding to the probable rupture location at a part that connects the tensile testing part and the first load applying piece, and that partitions the first load applying piece and the second end portion of the tensile testing part, and
    the second load applying piece includes
        an application surface that receives a load transmitted from the first end portion side toward the second end portion side; and
        a groove formed with a depth corresponding to the probable rupture location at a part that connects the tensile testing part and the second load applying piece, and that partitions the second load applying piece and the first end portion of the tensile testing part.

2. The test piece for tensile testing according to claim 1, wherein the first load applying piece and the second load applying piece are alternately arranged in a circumferential direction around the central axis.

3. The test piece for tensile testing according to claim 1, wherein the test piece for tensile testing is made of a fiber-reinforced composite material made with fibers as a base material, and a direction in which the fibers of the fiber-reinforced composite material do not extend is the pulling direction.

4. The test piece for tensile testing according to claim 2, wherein the test piece for tensile testing is made of a fiber-reinforced composite material made with fibers as a base material, and a direction in which the fibers of the fiber-reinforced composite material do not extend is the pulling direction.

5. A tensile testing method, comprising:
   applying loads in a direction along the central axis to the load applying pieces of the test piece for tensile testing according to claim 1 to exert a tensile force along the central axis.

\* \* \* \* \*